United States Patent [19]
Hasson

[11] Patent Number: 5,681,325
[45] Date of Patent: Oct. 28, 1997

[54] SUPPORT FOR SURGICAL INSTRUMENT

[76] Inventor: Harrith M. Hasson, 2043 N. Sedgwick, Chicago, Ill. 60614

[21] Appl. No.: 389,970

[22] Filed: Feb. 14, 1995

Related U.S. Application Data

[63] Continuation of Ser. No. 62,923, May 13, 1993, abandoned.

[51] Int. Cl.⁶ .................................................. A61B 17/42
[52] U.S. Cl. .................................................. 606/119
[58] Field of Search .................................. 606/119, 123, 606/190–198, 1, 108; 600/201, 204, 207

[56] References Cited

U.S. PATENT DOCUMENTS

| | | | |
|---|---|---|---|
| 1,856,295 | 5/1932 | Sovatkin | 606/119 |
| 2,374,863 | 5/1945 | Guttmann | 128/20 |
| 3,037,505 | 6/1962 | Walden et al. | 128/3 |
| 4,323,057 | 4/1982 | Jamieson | 600/201 |
| 4,585,438 | 4/1986 | Makler | 606/106 |
| 5,030,223 | 7/1991 | Anderson et al. | 606/130 |
| 5,047,036 | 9/1991 | Koutrouvelis | 606/130 |
| 5,147,372 | 9/1992 | Nymark et al. | 606/130 |
| 5,201,742 | 4/1993 | Hasson | 606/130 |
| 5,242,455 | 9/1993 | Skeens et al. | 606/130 |

FOREIGN PATENT DOCUMENTS 3314787  10/1984  Germany .................................. 128/3

OTHER PUBLICATIONS

California and Western Medicine 1936.

*Primary Examiner*—Glenn Dawson
*Attorney, Agent, or Firm*—Wood, Phillips, VanSanten, Clark & Mortimer

[57] ABSTRACT

A jig/support to consistently maintain a surgical instrument in a desired position within a vagina, uterus, or other body cavity, whether through a natural opening or an incision in the patient. The jig/support includes an instrument holder and structure cooperating between at least one of a support for a patient, a rigid base, and a patient and the instrument holder for maintaining the instrument holder in a preselected position relative to the one of the patient support, rigid base, and patient. An instrument held by the instrument holder can be controllably introduced and held consistently in a preselected, desired position within the body cavity.

9 Claims, 8 Drawing Sheets

FIG. 4
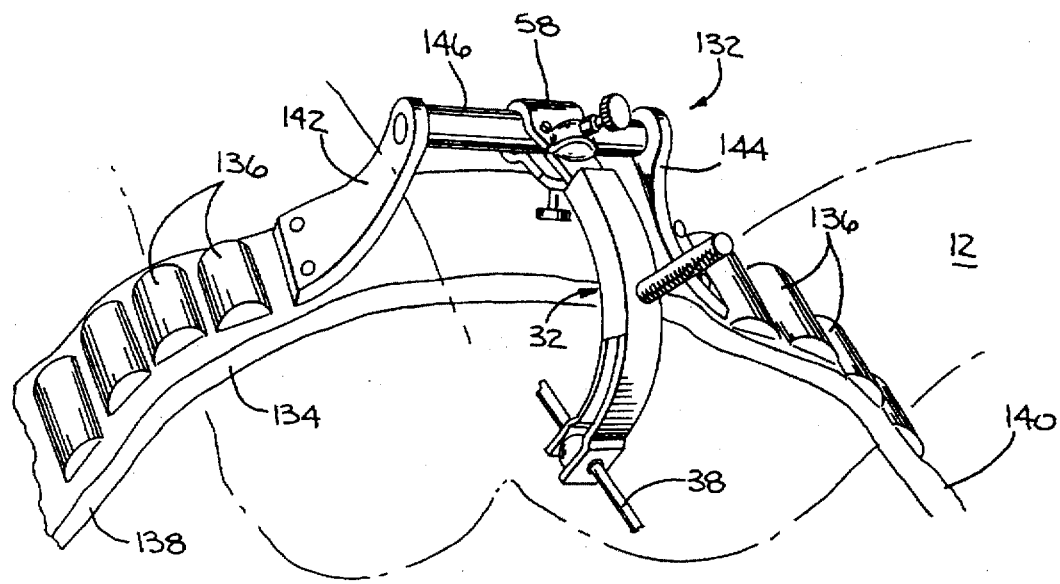
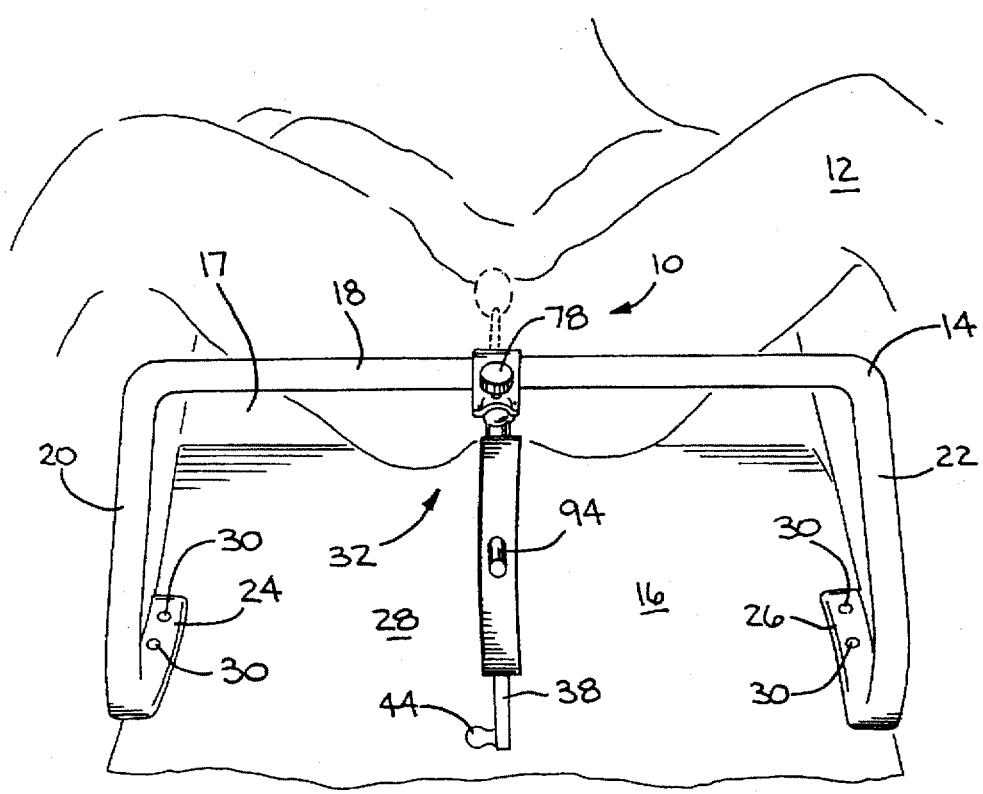
FIG. 5

SUPPORT FOR SURGICAL INSTRUMENT

This application is a continuation, of application Ser. No. 08/062,923, filed May 13, 1993, now abandoned.

BACKGROUND OF THE INVENTION

1. Field of the Invention

This invention relates to surgical instruments and, more particularly, to a jig/support for a) allowing controlled introduction of a surgical instrument into a body cavity and b) maintaining an instrument in a desired position within the cavity.

2. Background Art

It is common to perform a number of medical procedures in female patients without a large incision by using endoscopic techniques, to include a) laparoscopy to perform surgery on pelvic organs by passing a telescope (laparoscope) through a small abdominal incision (an artificial opening) to gain access to the pelvis and b) hysteroscopy to perform intrauterine surgery by introducing a telescope (hysteroscope) through the natural vaginal and cervical openings to access the uterus. In the case of laparoscopy, the surgeon always needs to use a dependable uterine manipulator to reposition the uterus to permit access to the region at which a procedure is to be performed. In the case of hysteroscopy, stabilizing and maintaining the position of the telescope within the uterus permits the surgeon to perform intrauterine procedures without fatigue and with precision.

Uterine manipulation may be effected during a procedure by the surgeon or by an assistant. It is difficult and counterproductive for the surgeon to both reposition the uterus with an instrument in one hand and perform the procedure through a separate instrument held by the other hand.

Further, because the uterus is flexible and tends naturally towards one orientation, the surgeon must constantly maintain a repositioning force on the uterus throughout the procedure. Not only is this activity tiring, but it is very difficult for the surgeon to maintain a consistent orientation of the uterus, particularly when the surgeon is simultaneously carrying out what is normally a delicate medical procedure.

The problem is aggravated when the surgeon is required to repeatedly withdraw an instrument and re-insert the same or a different instrument with the hand positioning the uterus. Upon withdrawal, the uterine manipulator is released, thereby allowing the uterus to relax to its normal state. The surgeon is then required to place the uterus back in the state it was before release, with the result being a loss of valuable time and energy. In fact, in advanced operative laparoscopy procedures, an assistant is required as it is not possible for the surgeon to perform the task of uterine manipulation as well as the intended procedures.

Even if the uterine manipulation is effected by an assistant, problems prevail. The assistant first of all takes up valuable space in an operating room and by being positioned in from of the surgeon between the legs of the patient may interfere with the surgeon's view of a monitoring TV.

It is equally difficult and wasteful for an assistant dedicated to only the one task to properly position, and maintain the desired position of, the uterus throughout a surgical procedure. This is because certain uterine positions are difficult to maintain with manual pressure and because conventional manipulators do not lend themselves to automatically holding uterine position, thereby requiring constant manual pressure which is awkward and causes fatigue.

In the event that the desired position of a uterus is not maintained, tension on the tissues is affected and access to the region at which a procedure is to be performed is impaired, complicating and undesirably lengthening the time necessary for the procedure. The surgeon also risks damaging adjacent tissues and organs because of lack of proper visualization and absence of tension on the affected tissue planes.

SUMMARY Of THE INVENTION

The present invention is specifically directed to overcoming the above enumerated problems in a novel and simple manner.

According to the invention, a jig/support is provided to consistently maintain a surgical instrument in a desired position within a vagina, uterus, or other body cavity, whether through a natural opening or an incision in the patient. The jig includes an instrument holder and structure cooperating between at least one of a support for a patient, a rigid base, and a patient and the instrument holder for maintaining the instrument holder in a preselected position relative to the one of the patient support, rigid base, and patient. An instrument held by the instrument holder can be controllably introduced and held consistently in a preselected, desired position within the body cavity.

By using a manipulator, such as a uterine manipulator, the uterus can be optimally positioned for performance of a medical procedure. The surgeon can introduce and withdraw instruments and perform surgery at will without disturbing the position of the uterus. This simplifies medical procedures, makes these procedures safer, and obviates the need for an assistant.

For greater versatility, the maintaining structure for the instrument holder maintains the instrument holder in a plurality of different positions.

In one form, the maintaining structure for the instrument holder has a base and an adjustable linkage connecting between the base and the instrument holder.

The adjustable linkage can take a wide variety of forms, including linkage members with universal connection therebetween, and connections that cause prescribed relative movement between the linkage members.

In one form, a first linkage member is connected to a second linkage member for one of universal movement and movement in a prescribed path, which path may be straight, arcuate, etc. The instrument holder can in mm be connected to at least one of the first and second linkage members.

The linkage members may be locked relative to each other and the base to securely fix the instrument holder in a plurality of different positions.

The universal connection between the linkage parts and base can be a ball and socket connection. A cooperating pin and slot connection can be used to guide relative movement of parts in a prescribed path.

A graspable handle can be provided on one or more of the linkage members to facilitate positive repositioning thereof without fatigue.

The instrument holder can have a clamp, or other structure, to selectively hold and release instruments of different types.

The base can be a weighted yoke to straddle part of a patient such as the torso or one or more limbs. The weight gives stability to the base. Alternatively, the base can be set directly upon a support for a patient. The base may be stable without connection to the support. Alternatively, the base can be bolted to or otherwise secured to the support.

Still further, the support may be in the form of a heavy weighted speculum having a part introduced into one of the patient's body cavities, such as the vagina. The speculum is supported and maintained in a desired position by gravity. In this form, the support has a base with a tongue to bear against tissue on a patient. The base has an elongate body with the tongue projecting in cantilever fashion from the base to allow it to penetrate a body cavity/opening. The tongue makes an angle with the length of the base that is no greater than 90° and, more preferably, less than 90°.

The body of the base supports the instrument holder which, in one form, is a ball and socket connector. The ball and socket can be moved relative to the tongue to make the jig/support more versatile.

The invention further comprehends a method of maintaining a surgical instrument in a desired position relative to a patient. The tongue on the jig/support on the last described embodiment is directed into a body cavity/opening so as to be supported on tissue in the vicinity of the body cavity/opening. An instrument can be placed in a holder on the body of the jig/support to be maintained in a desired position relative to a patient.

BRIEF DESCRIPTION OF THE DRAWINGS

FIG. 4 is a perspective view of a jig/support for an instrument according to the present invention with a modified form of base and in an operative position relative to a patient;

FIG. 5 is a front perspective view of the jig/support in FIG. 1 shown attached to a support for a patient and in an operative position relative to a patient;

DETAILED DESCRIPTION OF THE DRAWINGS

Figure 1:
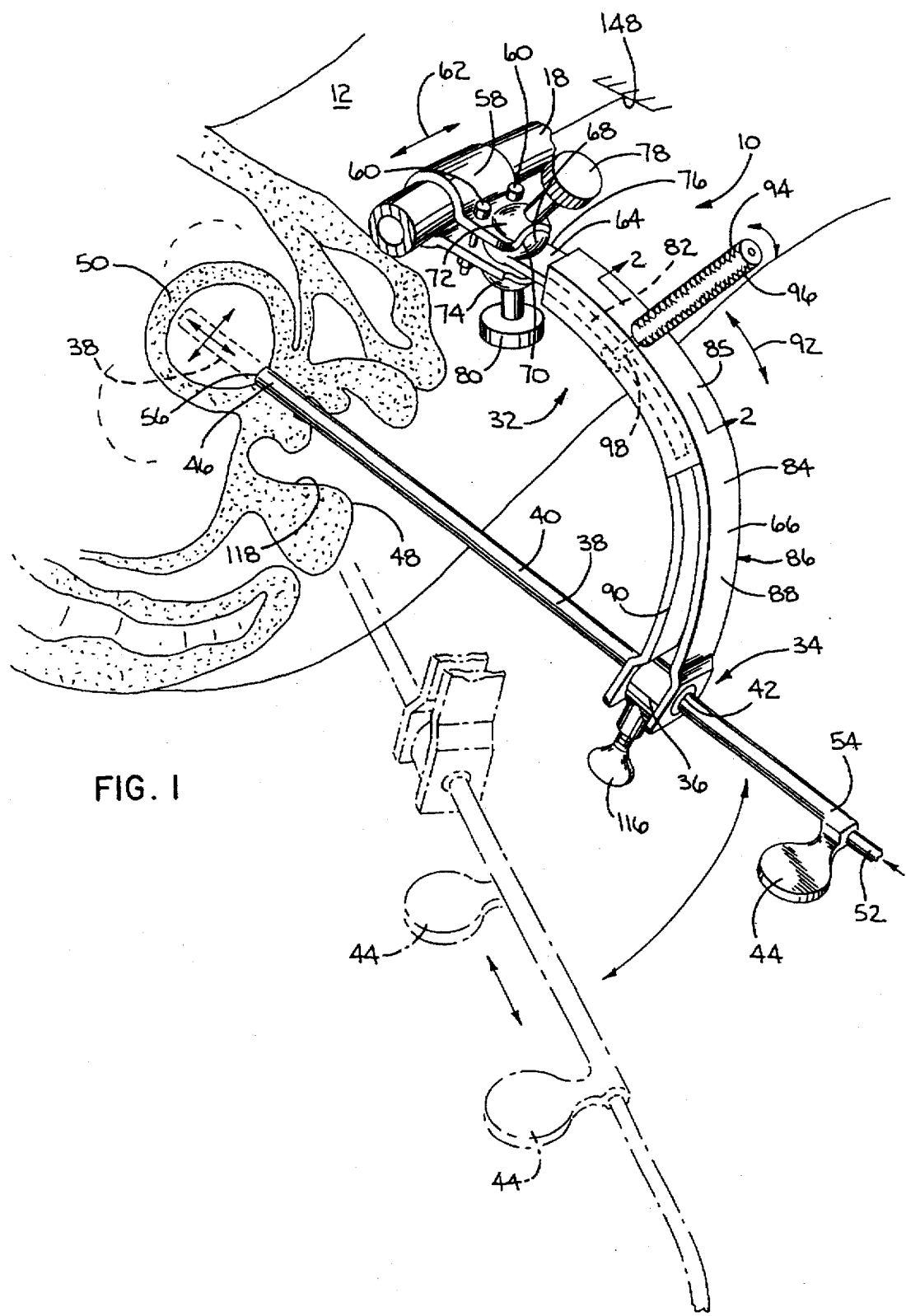
FIG. 1 is a perspective view of a jig/support, according to the present invention, with a surgical instrument in a holder thereon, and in an operative position relative to a patient.

In FIGS. 1, 2, 3 and 5, one form of jig/support, for a surgical instrument, according to the present invention, is shown at 10. The jig/support 10 is contemplated for use to assist in the performance of a variety of different surgical procedures, particularly those performed in or adjacent to a cavity accessed through either a natural body opening or an incision. The jig/support 10 is shown in the Figures herein as it would be used to assist an intrauterine hysteroscopic procedure performed on a patient 12. It should be understood that this particular application is not limiting, and is used only for purposes of illustration.

The jig/support 10 consists of a base 14 which is attached to a downwardly inclined leg section 16 of an operating room table 17 upon which the patient 12 is supported. When the leg section 16 is lowered into the lithotomy position for operative endoscopy, the base 14 projects from the leg section 16. The base 14 has an inverted, U-shaped configuration with a horizontal member 18 and laterally spaced vertical legs 20, 22 which have undermined free ends 24, 26, respectively, which rest upon an upwardly facing support surface 28 on the table 16. Bolts 30 may be used to fix the base 14 to the table 16 so that it does not slip during use. Alternatively, a secure brace may be used to attach the base 14 to the table 17.

The member 18 on the base 14 supports an adjustable linkage 32, which carries, at its free end 34, an instrument holder 36.

The instrument 38 shown is intended to be genetic in nature and is used only to describe the operation of the jig/support 10. The instrument 38 has an elongate body 40 which is directed through a bore 42 in the instrument holder 36 so as to be slidable in and out lengthwise relative to the instrument body 40. An enlarged tab 44 is integrally formed with the body 40 to facilitate reorientation of the instrument 38.

The instrument 38 may be any of a wide variety of surgical instruments. It may be, for example, a hysteroscope, a sleeve, or an intrauterine manipulator, having a free end 46 which can be directed through the vaginal opening 48 of the patient 12 and into the uterus 50 to effect repositioning and stabilization thereof or to effect repositioning and stabilization of the instrument 38 and free end 46 thereof within the uterine cavity. For example, the body 40 on the instrument 38 can be a hollow sleeve to allow guided insertion of another type of instrument 52 from the proximal end 54 through the body 40 to externally of the distal end 56 and into the uterus 50.

The linkage 32 is supported from the member 18 by a bracket 58. The bracket 58 surrounds the base member 18 and is clamped thereto, as by bolts 60. The bolts 60 can be loosened to allow the bracket 58, and thus the linkage 32 thereon, to be shifted laterally in the direction of the double-headed arrow 62.

The linkage 32 is, in the embodiment shown, made up of first and second linkage members 64, 66. The first linkage member 64 is connected to the bracket 58 for controlled movement relative thereto, while the second linkage member 66 is in turn connected to the first linkage member 154 for movement relative thereto.

The first linkage member 154 has a ball connector 68 that is guidingly received in a socket 70 defined by cooperating, semi-spherical walls 72, 74 on the bracket 58. The ball 68 and walls 72, 74 cooperatively make a ball and socket connection which allows universal relative movement between the end 76 of the first linkage member 64 and the bracket 58.

Thumb screws 78, 80 are threaded through the walls 72, 74, respectively, to engage the ball 68 to thereby lock the linkage end 76 to the bracket 58 in virtually an infinite number of different positions.

The first linkage member 64 has an arcuately-shaped body 82 which has a curvature matched to the body 84 of the second linkage member 66. The second linkage member 66 has a hollow, squared body section 85 over part of its length and a bifurcated end 86, remote from the bracket 58, defined by walls 88, 90.

Figure 2:
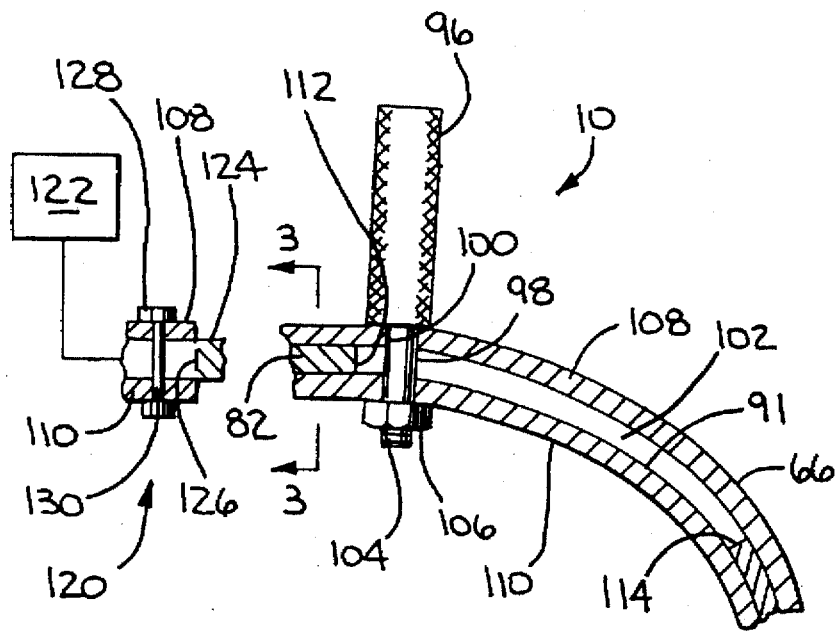
FIG. 2 is a cross-sectional view of cooperating linkage members on the jig/support taken along line 2—2 of FIG. 1 and showing a modified form of connection between the linkage members and a supporting base.
Figure 3:
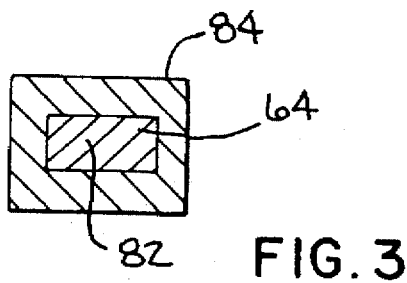
FIG. 3 is a cross-sectional view of the linkage members taken along line 3—3 of FIG. 2.

As seen in FIGS. 2 and 3, the hollow portion 85 of the body 84 defines a receptacle 91 matched to the cross section of the body 82 of the first linkage member 64. In this case, the matched cross sections are rectangular. Since the curvature of the bodies 82, 84 is the same, the first and second linkage members 64, 66 are allowed to slide lengthwise relative to each other in an arcuate path. By relatively moving the first and second linkage members 64, 66 in the prescribed arcuate path, indicated by the double-headed arrow 92, the combined effective length of the linkage members 64, 54, 66 can be changed.

To assist movement of the second linkage member 66 relative to the first linkage member 64, and to facilitate manipulation of the instrument 38, as to raise or lower the uterus 50 during a procedure, a handle 94 is provided. The handle 94 has a knurled, cylindrical body 96 with a threaded stem 98 that projects through a bore 100 in the second linkage member 66 and a coinciding, elongate slot 102 in the first linkage member 64. The stem 98 projects fully through the second linkage member 66 to have an exposed end 104 to which a nut 106 is attached. By tightening the handle 94, through rotation thereof, the body 82 of the first linkage member 64 is squeezed between spaced walls 108, 110 on the body 84 of the second linkage member 66 to thereby fix the relative lengthwise positions of the first and second linkage members 64, 66.

The slot 102 has a sufficient length that the combined length of the linkage members 64, 66 can be varied by several inches. The stem 98 abuts the slot ends 112, 114 to define the limits of relative movement between the first and second linkage members 64, 66.

With the above structure, it can be seen that several degrees of movement of the instrument 38 within the holder 36 are possible. The linkage 32 is shiftable with the bracket 58 laterally relative to the base 14 as a unit. The first and second linkage members 64, 66 are movable together universally about the ball 68 relative to the bracket 58. The instrument 38, as shown in phantom lines in FIG. 1, is in an exemplary position for uterine manipulation during a laparoscopic procedure. The second link member 66 can be raised and lowered in an arcuate path relative to the first linkage member 64 within the range permitted by the slot 102. The instrument 38 is moved lengthwise of itself within the holder 36 so that its distal end 56 abuts the top of the uterus 50 for effective mobilization of the uterus.

When this desired orientation of the instrument 38 is established, the user tightens a set screw 116, which locks the instrument 38 relative to the holder 36. Tightening of the handle 94 fixes the first and second linkage members 64, 66 relative to each other. Tightening of the set screws 78, 80 fixes the position of the first linkage member 64 relative to the bracket 58. Readjustment of the instrument 38 can be accomplished by selectively loosening the set screws 78, 80, 116 and handle 94 sufficiently to allow repositioning of the linkage members 64, 66 and instrument 38.

It can be seen that the instrument 38 is held stably in a desired orientation. Since the base 14 is substantially rigidly supported upon the table 16 which supports the patient 12, the instrument 38 can be consistently introduced to a body cavity and securely maintained in a desired position, as to position a uterus 50 in anticipation of the performance of a procedure. This frees the surgeon to perform laparoscopic surgery in the pelvis without using an assistant attending to the uterine manipulator, and to reposition the uterus easily from a normal standing position at the side of the operating room table. During hysteroscopic procedures, the surgeon may direct instruments through the body 40 of the instrument 38. During colposcopy, the surgeon may use an entirely separate instrument in the vagina 118, outside of the generic instrument 38.

A modified form of connection between the second linkage member 66 and first linkage member 64 is shown in FIGS. 2 at 120 to add another dimension to the movement of the instrument 38. In the connection 120, a ball connector 122 has a tongue 124 with an elongate slot 126 therein. The tongue 124 is captive between the walls 108, 110 of the second linkage member 66 and is secured by a bolt 128. By loosening the bolt 128, the tongue 124 is allowed to slide between substantially straight portions of the walls 108, 110, with the bolt stem 130 guiding relative movement between the tongue 124 and second linkage member 66 in the slot 126. This arrangement allows relative fore and aft movement between the linkage 32 and bracket 58 in substantially a horizontal direction.

A modified form of base, for supporting the linkage 32 and bracket 58, is shown at 132 in FIG. 4. The base 132 has an inverted U-shaped body 134 which is flexible to allow it to be draped over and conformed to the lower abdominal region of the patient 12. The body 134 has weights 136 thereon which draw the free ends 138, 140 downwardly to bear the body 134 conformingly and positively against the patient 12.

Curved plates 142, 144 project upwardly from the body 134 and support a horizontal member 146 therebetween. The member 146 carries the bracket 58 in the same manner as the member 18 in the previously described embodiment 10. The bracket 58 is connected to the member 146 in precisely the same manner as it is connected to the member 18 and in all other respects operates in the same manner.

The base 132 is supported on the patient 12 and provides a solid support for the bracket 58 and linkage 32 so that the instrument 38 can be maintained positively in any desired position.

It should be understood that a rigid base 148, shown schematically in FIG. 1, and situated in any of a number of different locations, can serve as a foundation to mount the bracket 58 upon. For example, the base 148 can be a wall, floor, ceiling, or a separate table.

Figure 6:
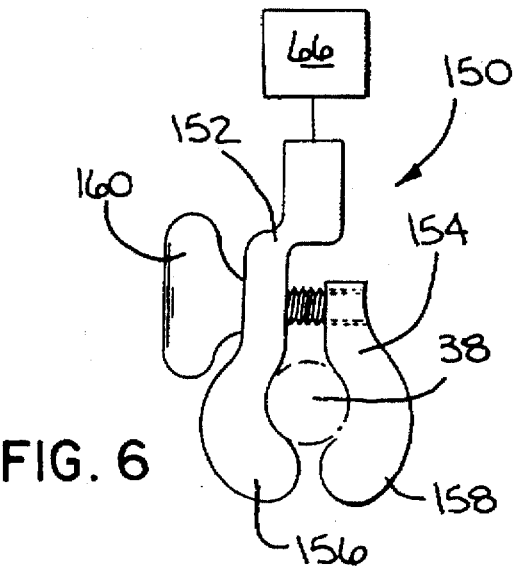
FIG. 6 is an elevation view of a releasable clamp for the instrument holder on the jig/support.

Another feature of the present invention is the provision of a readily releasable instrument clamp at 150 in FIG. 6. The clamp 150 is connected to the second linkage member 66 by any suitable means. The clamp 150 has cooperating first and second parts 152, 154 having jaws 156, 158 which are movable towards and away from each other by a screw 160. By simply loosening the screw 160, the jaws 156, 158 move away from each other to allow introduction or removal of the instrument 38. By tightening the screw 160, the instrument 38 is positively captured. The jaws 156, 158 can have sufficient width that there is no tendency of the instrument 38 to cant once it is clamped.

Another form of instrument jig/support, according to the present invention, is shown at 200 in FIGS. 7–11. The support 200 has a base 202 that is configured to be stabilized on the patient 204. Instead of being draped across the patient 204 as the base 132 is, as shown in FIG. 4, the support 202 has an offset tongue 210 which can be directed through the vaginal opening 212 to be supported on the vaginal wall 214. A weight 216, toward the bottom of the base 202, bears the bottom edge 218 of the tongue 210 firmly against the vaginal wall 214 so that the tongue 210 becomes partially enveloped by the vaginal wall 214 so that shifting thereof is minimized.

The base 202 carries an instrument holder 220 shown with a generic type of elongate instrument 222 operatively connected to the holder 220 to be universally pivotable relative to the base 202.

More particularly, the base 202 has an elongate body 224 extending substantially in a vertical direction. The body 224 has a first part 226, made from a member having a U-shaped cross section. The first part 226 has a vertical portion 228 which blends into the tongue 210 which is bent to make an angle α with the vertical potion 228. Preferably the angle α is less than 90° so that the free end 230 of the tongue 210 digs into the vaginal wall 214 under the weight of the support 200 to prevent inadvertent withdrawal thereof. The free end 230 of the tongue has a convex leading surface 232 which guides the tongue 210 with minimal interference through the vaginal opening 212.

The base 202 has a second part 234 that is straight and U-shaped and nests within the vertical portion 228 of the first base part 226. The first and second parts 226, 234 are fixed together by bolts 236 with nuts 238 threaded thereon so that the upper free end 240 of the second part 234 projects upwardly beyond the tongue 210 to accept the instrument holder 220.

The instrument holder 220 has an upwardly opening, cup-shaped receptacle 242 at the upper end 240 of the second base part 234. A U-shaped bracket 244 on the instrument holder 220 has one leg 246 projecting horizontally from the receptacle 242 and blending into a vertical base portion 248, which in turn blends into a second horizontal leg 250 that is substantially parallel to and spaced vertically from the leg 246. The leg 250 provides a support for a second, cupshaped receptacle 252, which opens downwardly towards the first receptacle 242.

A set screw 254 with an enlarged gripping handle 256 is threaded through the leg 250 and connects to the receptacle 252 so that turning of the handle 256 selectively moves the receptacle 252 towards and away from the receptacle 242. This arrangement is used to capture a ball connector 258 within a socket 260 defined cooperatively by the receptacles 242, 252. The ball connector 258 is thus pivotable universally within the socket 260.

The instrument 262 has a free end 264 with an enlargement 266 thereon to penetrate and support the uterus 268. Other types of instruments of course could be used consistently with the invention. The instrument 262 has an elongate body 270 which is extendable through a U-shaped, laterally opening slot 270 in the ball connector 258 into the operative position shown in FIGS. 7–11. By turning the handle 256 and thereby advancing the receptacle 252 down towards the receptacle 242, the ball connector 258 is captively fixed relative to the receptacles 242, 252 with the instrument 262 through the slot 270 in its desired position. At the same time, as the ball connector 258 is compressed between the receptacles 242, 252, the slot 270 is restricted so that the instrument 262 is maintained in the desired position and cannot escape from the slot.

Figure 7:
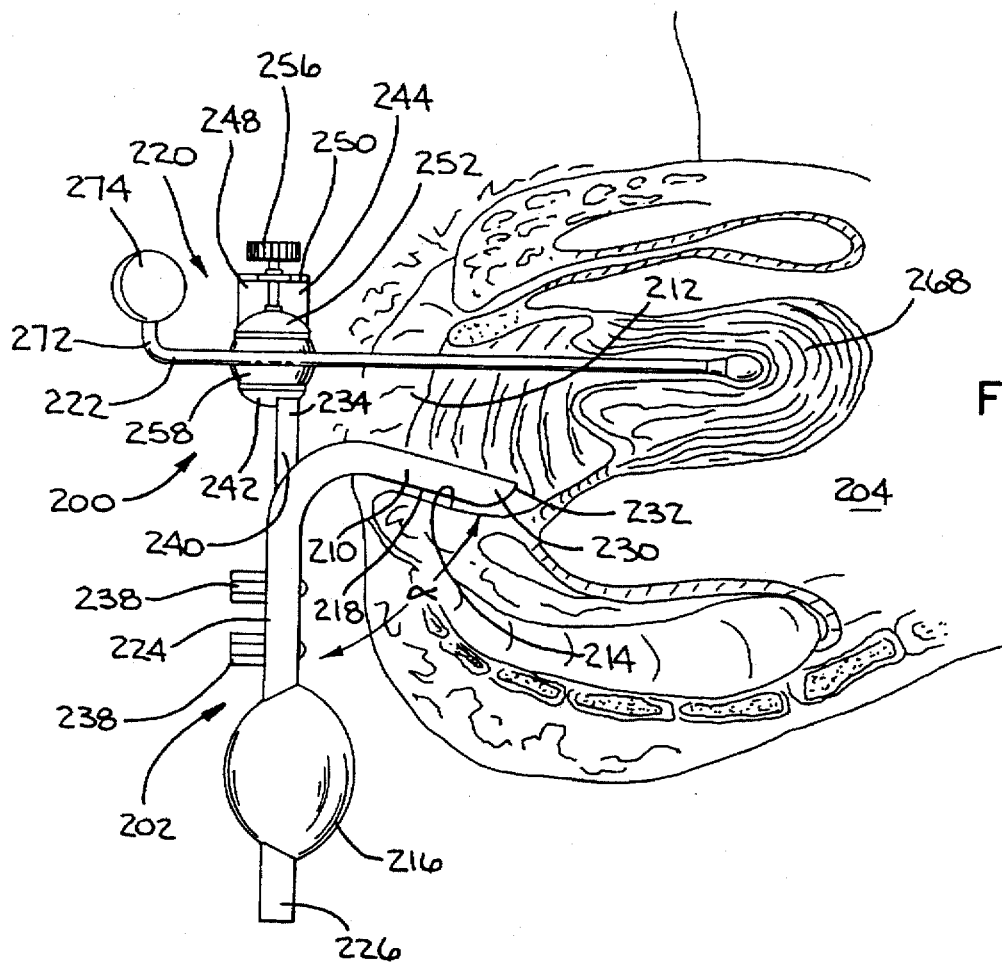
FIG. 7 is a side elevation view of a modified form of instrument jig/support, according to the present invention, and shown with an instrument thereon and operatively attached to a patient.
Figure 8:
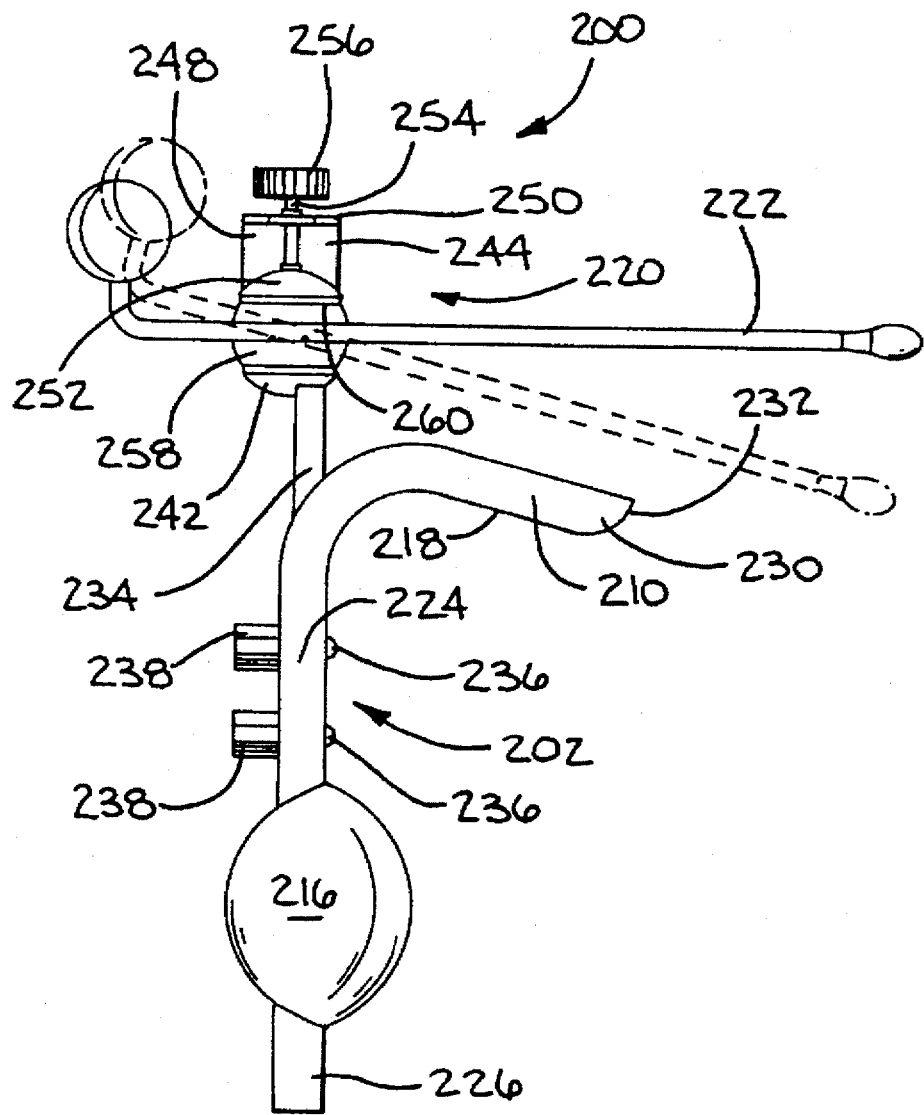
FIG. 8 is a side elevation view of the instrument jig/support of FIG. 7 with an instrument holder thereon shown in two different positions.
Figure 9:
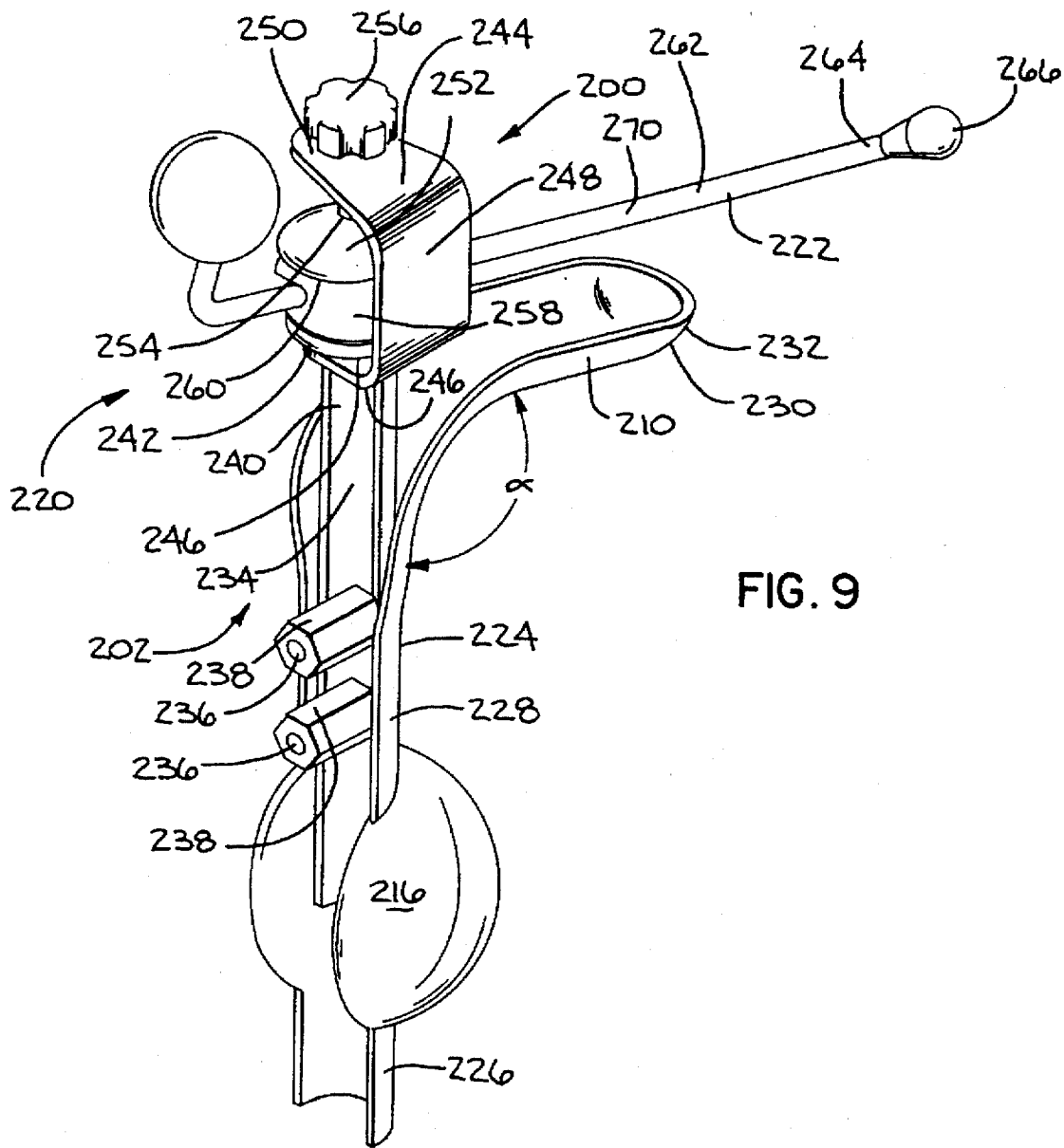
FIG. 9 is a rear perspective view of the instrument jig/support in FIGS. 7 and 8.
Figure 10:
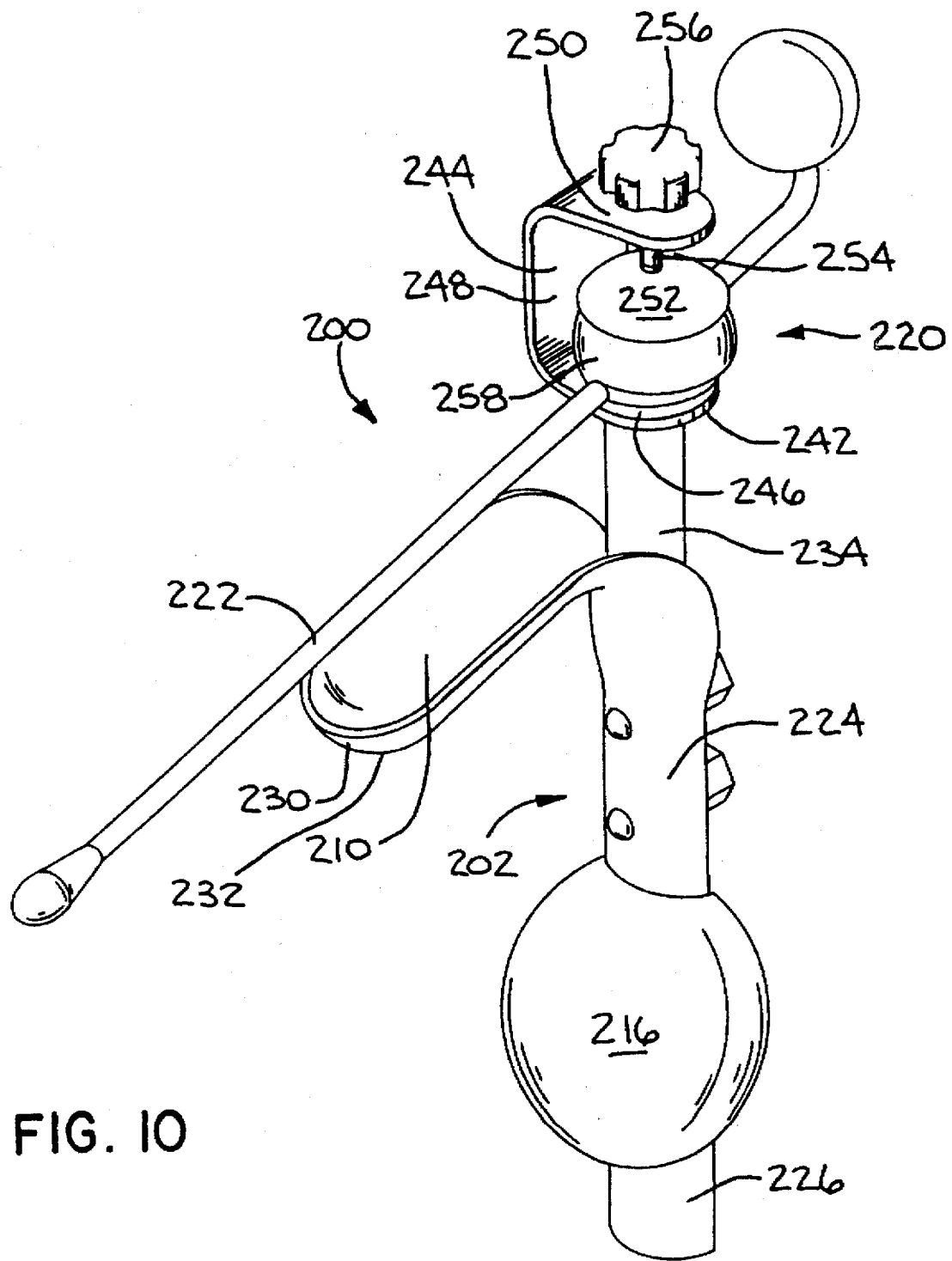
FIG. 10 is a front perspective view of the instrument jig/support in FIGS. 7-9.
Figure 11:
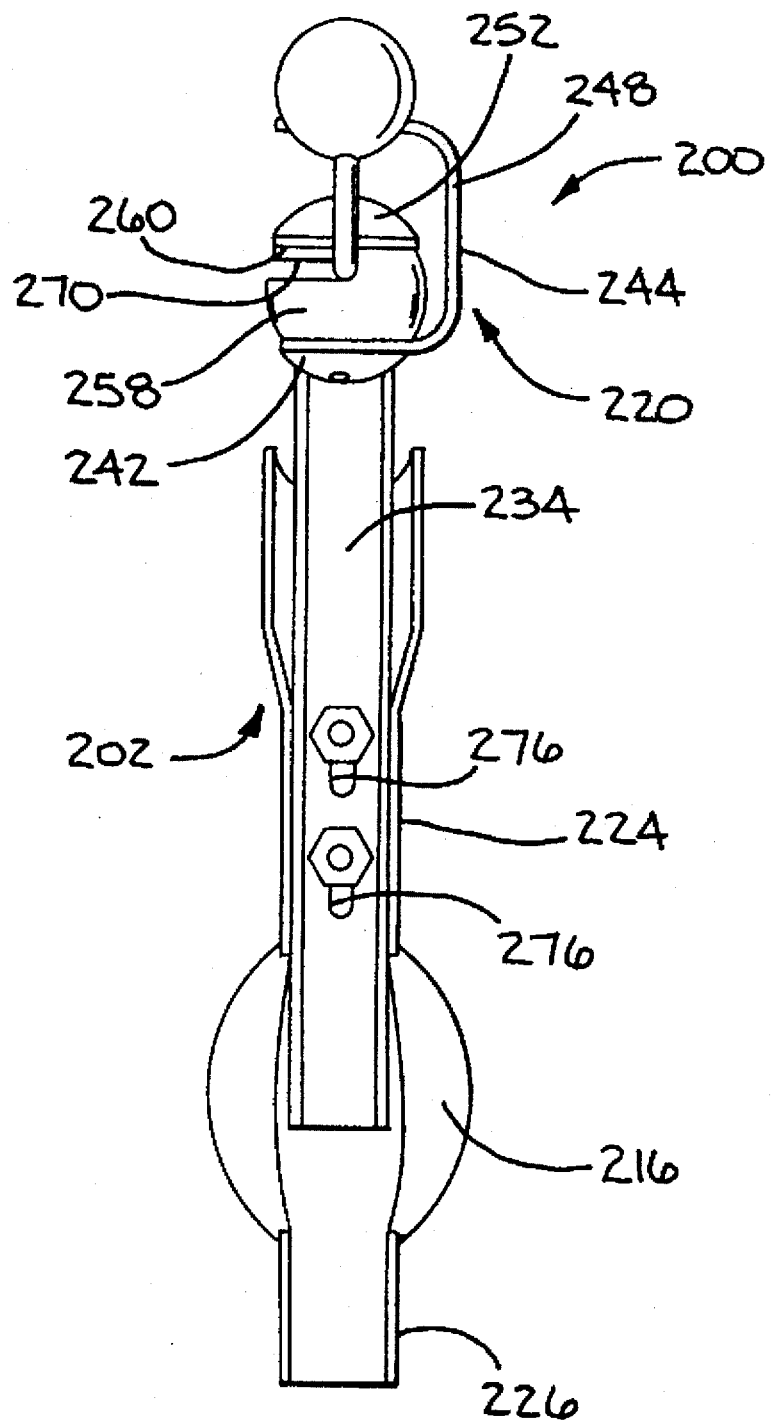
FIG. 11 is a rear elevation view of the instrument jig/support in FIGS. 7-10.

To operatively position the support 200, the user places the support 200, absent the instrument 262, in the operative position in FIG. 7. This is accomplished by merely advancing the tongue 210 through the vaginal opening 212 into the position shown in FIG. 7. The weight 216 is sufficient to bear the tongue 210 positively against the vaginal wall 214 so that the support 200 is rigidified sufficiently to positively support the instrument 262.

The handle 256 is rotated to loosen the set screw 254 sufficiently to allow the ball connector 258 to be placed in the socket 260. The handle 256 is then turned to hold the ball connector 258 in place while still allowing rotation thereof within the socket 260. Repositioning of the ball connector 258 and instrument 262 is facilitated by providing an offset end 272 on the instrument 262, with an enlargement 274 thereon that can be grasped to manipulate the instrument, as to reposition it to the phantom line position in FIG. 8. While the instrument 262 is preferably slidable into and out of the slot 270 in the ball connector 258, the ball connector 258 could be made with a fully surrounded through bore so that relative movement between the ball connector 258 and instrument 262 is limited to relative movement lengthwise of the instrument 262. Once the instrument 262 is in the desired position, the handle 256 is turned to lock the ball connector 258 between the receptacles 242, 252.

Vertical adjustment of the second base part 234 relative to the first part 226 is permitted by providing vertically extending, elongate slots 276 in at least one of the parts 226, 234. This allows changing of the vertical position of the ball connector 258 relative to the tongue 210 and thus changing of the vertical position of the instrument 262 on the ball connector 258 relative to the vagina upon which the support 200 is carried.

With the inventive structure, the surgeon can positively and consistently support an internal organ which frees the surgeon to perform whatever procedure is desired within the general body cavity in which the organ lies or in a cavity defined by the organ itself. Surgical procedures can thus be performed more quickly, more safely and more effectively than can be accomplished with conventional equipment.

The foregoing disclosure of specific embodiments is intended to be illustrative of the broad concepts comprehended by the invention.

I claim:

1. A support for maintaining a surgical instrument in a desired position within a body cavity of a patient, said support comprising:

means for holding an elongate instrument so that the length of an elongate instrument held by the holding means can be projected away from the support;

a base; and means cooperating between the base and instrument holding means for locking the instrument holding means in a plurality of different positions relative to the base as an incident of which an instrument held by the instrument holding means is placed selectively in a plurality of different positions, said base including a cantilevered tongue to be projected into a body cavity on a patient to support the base on tissue of a patient surrounding the body cavity, said cooperating means comprising means for allowing an instrument held by the instrument holding means to be moved pivotably about more than one axis relative to the tongue.

2. The surgical instrument, support according to claim 1 wherein the instrument holding means includes a clamp for releasably holding a surgical instrument.

3. The surgical instrument support according to claim 1 wherein the base further includes an elongate body and the tongue projects angularly with respect to the length of the elongate body so as to make an angle of no greater than 90° with the length of the elongate body.

4. The surgical instrument support according to claim 1 wherein the instrument holding means includes a ball and socket connection to allow guided universal movement of an instrument held by the instrument holding means relative to a patient.

5. The surgical instrument, support according to claim 4 wherein said cooperating means include means for selectively varying the relative positions of the ball and socket connection and the tongue.

6. A support for maintaining a surgical instrument in a desired position within a body of a patient, said support comprising:

means for holding an instrument to be directed into a body opening;

a base;

means on the instrument holding means to allow an instrument to be guidingly repositioned relative to the instrument holding means and releasably locked in a plurality of differently positions relative to the instrument holding means, said base comprising an elongated body with a tongue projecting angularly to the length of the elongated body to be directed into a body cavity to bear upon tissue surrounding a body cavity; and means cooperating between the base and instrument holding means comprising a ball and socket connection for allowing an instrument held by the instrument holding means to be moved consistently in a predetermined path relative to the tongue into a plurality of different positions.

7. The surgical instrument support according to claim 6 wherein the tongue projects angularly from the body so as to make an angle of no greater than 90° with the length of the body.

8. The surgical instrument support according to claim 6 wherein the tongue projects in a first direction away from the elongate body and the tongue projects further from the elongate body in the first direction than any part of the support projects away from the elongate body oppositely to the first direction.

9. The surgical instrument support according to claim 8 wherein the elongate body has a top and bottom and there is a weight on the elongate body below the tongue to urge the tongue against a supporting tissue.

* * * * *